United States Patent [19]
Goedeke

[11] Patent Number: 5,904,708
[45] Date of Patent: May 18, 1999

[54] SYSTEM AND METHOD FOR DERIVING RELATIVE PHYSIOLOGIC SIGNALS

[75] Inventor: Steven D. Goedeke, Forest Lake, Minn.

[73] Assignee: Medtronic, Inc., Minneapolis, Minn.

[21] Appl. No.: 09/044,613

[22] Filed: Mar. 19, 1998

[51] Int. Cl.[6] .................................................. A61N 1/365
[52] U.S. Cl. .............................................................. 607/18
[58] Field of Search ...................... 607/2, 9, 18; 600/509

[56] References Cited

U.S. PATENT DOCUMENTS

| | | |
|---|---|---|
| 4,407,296 | 10/1983 | Anderson . |
| 4,436,092 | 3/1984 | Cook et al. . |
| 4,494,950 | 1/1985 | Fischell . |
| 4,524,773 | 6/1985 | Fischell et al. . |
| 4,791,931 | 12/1988 | Slate . |
| 4,899,751 | 2/1990 | Cohen . |
| 4,987,897 | 1/1991 | Funke . |
| 5,113,859 | 5/1992 | Funke . |
| 5,113,869 | 5/1992 | Nappholz et al. . |
| 5,330,505 | 7/1994 | Cohen . |
| 5,368,040 | 11/1994 | Carney . |
| 5,487,752 | 1/1996 | Salo et al. . |
| 5,535,752 | 7/1996 | Halperin et al. . |
| 5,540,727 | 7/1996 | Tockman et al. . |
| 5,564,434 | 10/1996 | Halperin et al. . |

*Primary Examiner*—Scott M. Getzow
*Attorney, Agent, or Firm*—Reed A. Duthler; Harold R. Patton

[57] ABSTRACT

A patient monitoring and/or therapy delivery system and method employing an implantable medical device for sensing absolute physiologic signal values within the body of a patient, e.g., absolute blood pressure, temperature, etc., and an external monitoring device for monitoring and conveying ambient signal values to the implantable medical device, wherein the absolute physiologic signal values and the ambient signal values are combined to derive relative physiologic signal values for storage and/or control of a therapy provided by the implantable medical device. In the context of an implantable physiologic monitor, the relative and optionally, the absolute and/or ambient physiologic signal values are stored in memory for telemetry out to an external programmer in an uplink RF telemetry transmission initiated by medical personnel operating the external programmer. In the context of an implantable therapy delivery device, the relative physiologic signal values are also employed in therapy delivery algorithms.

44 Claims, 6 Drawing Sheets

SYSTEM AND METHOD FOR DERIVING RELATIVE PHYSIOLOGIC SIGNALS

FIELD OF THE INVENTION

The present invention pertains to a patient monitoring and/or therapy delivery systems and methods, and more particularly to employing an implantable medical device for sensing absolute physiologic signal values within the body of a patient, e.g., absolute blood pressure, temperature, etc., an external monitoring device for monitoring and conveying ambient signal values to the implantable medical device, and combining the absolute physiologic signal values and the ambient signal values to derive relative physiologic signal values for storage and/or control of a therapy provided by the implantable medical device.

BACKGROUND OF THE INVENTION

A great many implantable systems for cardiac monitoring and/or therapy comprising sensors located in a blood vessel or heart chamber coupled with an implantable monitor or therapy delivery device have been proposed or implemented. For example, such cardiac systems include implantable heart monitors and therapy delivery devices including pacemakers, cardioverter/defibrillators, cardiomyostimulators, and drug delivery devices. All of these systems include electrodes for sensing and sense amplifiers for recording and/or deriving sense event signals from the intracardiac or remote electrogram (EGM). In current implantable cardiac devices providing a therapy, the sense event signals are utilized to control the delivery of the therapy in accordance with an operating algorithm and at least selected EGM signal segments and sense event histogram data or the like are stored in internal RAM for telemetry out to an external programmer at a later time. In implantable cardiac monitors, e.g., the MEDTRONIC® Reveal implantable heart monitor, a 42 minute segment of EGM is recorded when the patient activates it, by applying a magnet over the site of implantation, in response to feeling the effects of an arrhythmic episode.

Such implantable medical devices that provide a therapy and/or monitor a physiologic condition or state are programmable and/or can be interrogated by an external programmer through the use of bidirectional RF telemetry that exchanges data and commands via uplink and downlink RF telemetry transmissions through the patient's skin. A great many telemetry schemes have been employed and proposed by the assignee, Medtronic, Inc., that typically involve short range telemetry transmissions employing a 175 kHz RF carrier and close physical coupling of magnetic fields encompassing the RF telemetry antenna coils of the implanted medical device and a programming head placed against the patient's skin. A great many other telemetry systems have been proposed to achieve longer range, yet secure, RF telemetry between implantable and external monitoring devices as described, for example, in U.S. Pat. No. 5,113,869 and in commonly assigned U.S. patent application Ser. No. 08/900,624 filed Jul. 25, 1997, for IMPLANTABLE MEDICAL DEVICE MICROSTRIP TELEMETRY ANTENNA in the names of Weimin Sun et al., both incorporated herein by reference.

In addition, various other communication systems have been proposed to effect communication of data and commands between external, body worn, medical devices and implantable medical devices. In U.S. Pat. Nos. 5,487,752 and 5,540,727, assigned to Cardiac Pacemakers, Inc., systems are disclosed for optimizing the function of an implantable medical device by employing remote sensor modules for measuring parameters related to cardiac performance and deriving programming commands for optimizing the operating modes and parameters of the implantable medical device using a telemetry system providing uplink and downlink RF telemetry transmissions therebetween and through the patient's skin.

Moreover, several systems are disclosed for communicating between primary implantable or skin contacting devices and secondary implantable or skin contacting devices using the body as a communication medium as disclosed in U.S. Pat. Nos. 4,524,773, 4,494,950, 4,987,897, and 5,113,859, all incorporated herein by reference. In certain of these patents, secondary remotely implanted or skin worn physiologic sensor modules are described for sensing particular physiologic conditions or states to derive remote sense signals representative thereof. The sensor modules encode the remote sense signals for transmission and transmit the encoded remote sense signals to the primary implantable medical device for processing and use in an algorithm controlling the delivery of a therapy either by the primary implantable medical device or another secondary, therapy delivery, implantable medical device.

Efforts have also been underway for many years to develop implantable physiologic signal transducers and sensors for temporary or chronic use in a body organ or vessel usable with such implantable medical devices for monitoring a physiologic condition other than or in addition to the EGM to derive and store data and/or to control a therapy delivered by the implantable medical device. In respect to cardiac monitoring, it has been proposed to sense and record such additional physiologic signals including blood pressure in or adjoining blood vessels and heart chambers during the cardiac cycle, blood temperature, pH, and a variety of blood gases. Implantable heart monitors and blood pressure and temperature sensors that derive absolute blood pressure signals and temperature signals are disclosed in commonly assigned U.S. Pat. Nos. 5,368,040, 5,535,752 and 5,564,434, and in U.S. Pat. No. 4,791,931, all incorporated by reference herein. A comprehensive listing of implantable therapy delivery devices are disclosed in conjunction with implantable sensors for sensing a wide variety of cardiac physiologic signals in U.S. Pat. No. 5,330,505, incorporated herein by reference. Numerous attempts have been made over the years to refine implantable blood pressure sensors that accurately reflect the actual changes in cardiac blood pressure as set forth in the above-incorporated, commonly assigned, '752 and '434 patents.

Blood pressure and temperature signal values respond to changes in cardiac output that may be caused by a cardiac failure, e.g., fibrillation or high rate tachycardia, or that may reflect a change in the body's need for oxygenated blood. In the former case, monitoring of a substantial drop in blood pressure in a heart chamber, particularly the right ventricle, alone or in conjunction with an accelerated or chaotic EGM, was proposed more than 30 years ago as an indicia of fibrillation or tachycardia sufficient to trigger automatic delivery of defibrillation or cardioversion shock. More recently, it has been proposed to monitor the changes in blood pressure (dP/dt) that accompany normal heart contraction and relaxation and blood pressure changes that occur during high rate tachycardia and fibrillation or flutter.

A number of cardiac pacing systems and algorithms for processing the monitored mean and dP/dt blood pressure have been proposed and, in some instances employed clinically, for treating bradycardia. Such systems and algorithms are designed to sense and respond to mean or dP/dt changes in blood pressure to change the cardiac pacing rate in a rate range between an upper and a lower pacing rate limit in order to control cardiac output. Similarly, a number of cardiac pacing systems have been proposed, e.g., the system disclosed in U.S. Pat. No. 4,436,092, incorporated herein by reference, and, in some instances employed clinically, that sense and respond to changes in blood temperature to change the cardiac pacing rate in a rate range between an upper and a lower pacing rate limit in order to control cardiac output.

Certain of the measured physiologic signals derived from the heart or blood in the circulatory system are affected by ambient conditions that cannot be separately measured by the implantable medical device. Specifically, blood pressure and temperature signal values derived by a wholly implantable system are affected by atmospheric pressure acting on the patient and ambient temperature or by a fever afflicting the patient, respectively. In addition, certain implantable blood pressure sensors, e.g., those disclosed in the above-incorporated, commonly assigned '434 and '752 patents, are also affected by blood temperature changes.

In commonly assigned U.S. Pat. No. 4,407,296, a pressure sensing lead is disclosed that attempts to account for the affect of atmospheric pressure by providing an air chamber behind the sensor diaphragm exposed to blood pressure that is either sealed at a known average atmospheric pressure or leads to a further membrane or diaphragm near the proximal end of the lead body that is to be positioned in the abdominal cavity where the implantable monitor or pulse generator is implanted. In practice, this approach has proven to be inadequate because the known pressure cannot account for changes in barometric pressure and renders the blood pressure measurements ambiguous and the membrane on the lead body is difficult to manufacture, fragile and can become obstructed in chronic implantation.

In the above referenced '505 patent and in the related U.S. Pat. No. 4,899,751 and other patents by the same patentee, long term and short term mean blood pressure values are derived from the same implantable sensor and combined in an attempt to predict the onset of a cardiac arrhythmia or to provide an indication of the patient's requirements for cardiac output. This approach has not proven to be capable of negating the effects of barometric pressure on the long term and short term mean blood pressure values.

The absolute blood pressure changes, including both mean or average blood pressure and dP/dt pressure changes that are sensed by the implantable pressure sensors are influenced by barometric pressure changes. For example, when a patient such an implantable blood pressure sensing medical device changes elevation by ascending or descending in an elevator in a tall building or in an airplane, the change in barometric pressure changes the absolute blood pressure sensed in the body by an amount that can mask changes that are sought to be measured. In the context of an implantable rate responsive pacemaker operating under a rate control algorithm, the pressure change caused by the elevation change itself may exceed the blood pressure change that reflects a change in exercise level of the patient and be mis-interpreted as meriting a change in pacing rate to the upper or lower pacing rate limit, which can, at least, be uncomfortable to the patient. The barometric pressure effect can similarly have a negative effect on operating and detection functions of other implantable medical devices reliant on accurately sensing cardiac blood pressure changes that truly reflect a cardiac function or requirement for cardiac output.

Barometric pressure acting on the body can also affect the operation of other implanted sensors, e.g., respiration sensors relying on the use of impedance plethysmography. A number of cardiac pacing systems have been proposed and, in some instances employed clinically, for treating bradycardia that sense and respond to changes in respiration as measured by impedance changes between electrodes spaced across the patient's thorax from which minute ventilation is derived. The impedance changes are quantified in time to derive a control signal for increasing or decreasing the cardiac pacing rate in a rate range between an upper and a lower pacing rate limit in order to control cardiac output. The impedance signal baseline and rate of change can be affected by the barometric pressure reflected in the patient's lungs which changes with weather and elevation changes made by the patient.

It has also been proposed to monitor respiration induced pressure waves from sampled absolute blood pressure values and to derive respiration rate therefrom. The sampled absolute pressure signal baseline and rate of change can be affected by the barometric pressure reflected in the patient's heart which also changes with weather and elevation changes made by the patient.

Conceptually, similar problems can accompany the reliance on blood temperature as an indicia of patient activity level, for example. A fever or a high ambient air temperature raising the blood temperature can be mis-interpreted as an indicia of elevated patient activity and be mis-interpreted by a therapy delivery device, e.g., a rate responsive cardiac pacemaker.

At this time, I am not aware of any practical way to measure the ambient air pressure affecting the sensed blood pressure or the ambient temperature affecting the sensed blood temperature and separate it from the internally sensed absolute pressure and temperature. In the context of implantable heart monitors of the type described above for measuring absolute blood pressure, the resulting data may be misleading or inconvenient to interpret by the physician. Physicians are accustomed to taking and interpreting external readings of blood pressure using apparatus that takes barometric pressure into account. For this reason, it is suggested in the above-incorporated, commonly assigned, '752 and '434 patents that the patient may be provided with a belt worn external pressure recorder that records and time stamps recordings of barometric pressure that can be retrieved and used for comparison with the internally recorded absolute blood pressure data.

Despite the considerable effort that has been expended in designing such implantable medical devices and associated sensors for sensing such physiologic signals, a need exists for a system and method for accounting for ambient conditions surrounding the patient that affect the sensed and measured physiologic signal values, particularly in the case of blood pressure and temperature.

SUMMARY OF THE INVENTION

It is therefore an object of the present invention to provide a system and method employed in an implantable medical device for combining absolute and ambient physiologic signal values to derive relative physiologic signal values for storage and/or control of a therapy provided by the implantable medical device.

It is a particular object of the present invention to provide a system and method for combining absolute blood pressure and barometric pressure signal values to derive relative blood pressure signal values for storage and/or control of a therapy provided by an implantable cardiac monitor or therapy delivery device.

Similarly, it is a further particular object of the present invention to provide a system and method for combining other absolute physiologic signal values with ambient signal values affecting the sensed absolute physiologic signal value to derive relative physiologic signal values for storage and/or control of a therapy provided by an implantable cardiac monitor or therapy delivery device.

It is yet a further object of the present invention to provide an implantable medical device monitoring system and method for accurately sensing absolute physiologic signal values within the body, e.g. blood pressure signals and/or temperature signals, an external monitoring device for sensing and conveying ambient signal values to the implantable medical device, and processing the sensed absolute physiologic signal values with respect to ambient signal values derived externally to the patient's body into relative physiologic signal values for storage in memory within the implantable medical device for telemetry out to an external medical device at a later time.

These and other objects of the present invention are realized in an implantable medical device monitoring system and method for accurately sensing absolute physiologic signal values within the body, e.g. blood pressure signals and/or temperature signals, and processing the sensed absolute physiologic signal values with respect to ambient signal values derived externally to the patient's body into relative physiologic signal values for storage within the implantable medical device. In accordance with the invention, the ambient signal values, e.g., barometric pressure and/or ambient temperature, are monitored in an externally worn sensor module or monitoring device and communicated to the implantable medical device for use therein.

The implantable medical device monitoring method and system for carrying out the method for deriving relative physiologic signal values for use and/or storage within the implantable medical device preferably comprises the sequentially performed steps of and means operable for: (1) in the implantable medical device, sensing a physiologic state or condition within the body of the patient; and deriving an absolute physiologic signal value from the sensed physiologic state or condition; (2) in an external monitoring device, sensing an ambient state or condition outside the body affecting the sensed physiologic state or condition within the body; deriving an ambient signal value from the sensed ambient state or condition; and conveying the ambient signal value from the external monitoring device to the implantable medical device; and (3) in the implantable medical device, combining the derived absolute physiologic signal value and the sensed ambient signal value to derive a relative physiologic signal value therefrom.

The external monitoring device preferably comprises an externally worn sensor module having the capacity to sense ambient signal values and periodically transmit them by a downlink RF telemetry transmission to the implantable medical device telemetry transceiver for use in the processing of sensed absolute physiologic signal values to derive relative physiologic signal values. In the context of an implantable physiologic monitor, the relative and, optionally, the absolute and/or ambient physiologic signal values are stored in memory for telemetry out to an external programmer in an uplink RF telemetry transmission initiated by medical personnel operating the external programmer. In the context of an implantable therapy delivery device, the relative physiologic signal values are also employed in therapy delivery algorithms to control the delivery of the therapy.

In the typical implantable monitor or therapy delivery device, communications with external medical equipment, e.g. an external programmer, are effected by uplink and downlink RF telemetry transmissions to convey data and programming or interrogation commands, respectively. It will be understood that the present invention contemplates that the sampling frequency and transmission frequency of downlink RF telemetry transmissions of the ambient signal values can be adjusted to fit the circumstances of the particular patient, the particular physiologic condition or state being monitored or the physiologic sensor so that the relative physiologic signal values are derived on a timely basis that is useful for monitoring or controlling therapy delivery. Downlink RF telemetry transmissions to and uplink RF telemetry transmissions from implantable medical devices consume battery power as the receiver and transmitter, respectively, are powered up. The implantable medical device typically samples physiologic signals on a relatively frequent basis either to gather data or to control therapy delivery in a timely manner, and this normal primary activity consumes battery power. In order to minimize the additional consumption of battery power in the implantable medical device while practicing the present invention, the frequency of downlink RF telemetry transmissions is preferably minimized, while retaining the ability to meaningfully employ the ambient signal value or values.

In the context of an implantable medical monitoring system, the absolute physiologic signal values are derived at a sampling frequency which may be related to the cardiac cycle, typical patient respiration rates, or the like, and stored in device memory registers allocated thereto on a FIFO basis. The absolute physiologic signal data is accumulated at the sampling frequency over a period of time that may be greater or shorter than the interval between conveyed ambient signal values. In one embodiment, a single ambient signal value is periodically sampled at a lower frequency, communicated to the implantable medical device, and combined with the accumulated absolute physiologic signal data to derive a relative physiologic data set.

However, it is preferred that the ambient signal values are derived at the same frequency as the absolute physiologic signal values and are also stored in sensor module memory registers on a FIFO basis. Then, after storage of a predetermined number of ambient signal values, all of the stored ambient signal values are communicated to the implantable medical monitoring device. Each ambient signal value is then combined with the corresponding (in time) stored absolute physiologic value to derive a relative physiologic signal value. The set of relative physiologic signal value data is then stored in device memory allocated to the storage of the most recent, retrospective, data set on a FIFO basis. The most recent relative physiologic signal value data set may include data for 1–7 days, for example. The data set is read out and conveyed via uplink RF telemetry to an external receiver at the point in time when the user or medical attendant initiates a downlink RF telemetry transmission of an interrogation command to the implantable medical device.

A date and time stamp may be appended to the most recent relative physiologic signal data for uplink RF telemetry with it in case the external monitoring device fails to operate and downlink RF telemeter the ambient signal value for some reason, e.g., depletion of its battery. Storage of any further data may be halted or absolute physiologic signal values may be stored until the data is read out.

The external monitoring device may also periodically transmit a time synchronization signal to the implantable medical device to reset its real time clock and synchronize it with the real time clock of the external monitoring device.

This feature ensures that the sampled absolute physiologic signal values are time correlated accurately with the ambient signal values that are transmitted from the external monitoring device. The time synchronization signal may be transmitted independently of or accompany the downlink RF transmission of the ambient signal values.

In the context of a therapy delivery device, a similar approach may be employed for deriving relative physiologic signal values for controlling device function. If appropriate, the relative physiologic data set that is calculated on transmission of the ambient signal values may be employed in the succeeding interval until the next downlink communication of ambient signal values to control device operations.

Alternatively, one or more successive ambient signal value received from the external monitoring device may be stored in implantable device memory for a predetermined time period at least as long as the time period between successive downlink RF telemetry transmissions of the ambient signal values. The stored ambient signal value may be combined with each derived physiologic signal value until it is replaced by an updated ambient signal value or until an "aging" timer times out. The aging time period is reset on receipt of each successive ambient signal value, but if it lapses, then the implantable medical device either halts the derivation of the relative physiologic signal values or tags the derived relative physiologic signal values as based on an "aged" ambient signal value. In the context of implantable therapy delivery devices, the therapy delivery algorithm may revert to a default mode in the event that the received ambient signal value becomes "aged".

It will be understood that the time period between successive downlink RF telemetry transmissions of ambient signal values may be greatly reduced if required under the circumstances or if energy considerations are not important or are overcome by higher efficiency reception of downlink RF telemetry transmissions or high capacity implantable device batteries or other improvements.

It should also be understood that an extrinsic event may be specified to trigger the sensor module to commence transmission of the ambient signal value for use in the implantable medical device. For example, consider an implantable cardioverter-defibrillator relying on relative blood pressure to augment detection of a malignant tachyarrythmia. The detection of a high heart rate may cause the implantable cardioverter-defibrillator to uplink RF telemeter a command to the sensor module to downlink RF telemeter the ambient signal level for combination with the sensed absolute blood pressure to determine. The derived relative blood pressure may be employed to confirm a diagnosis of a malignant tachyarryhmia.

The practice of the present invention in the context of an implantable physiologic monitor advantageously eliminates the need to make time based comparisons of the external ambient signal values continuously stored in a patient worn sensor module with the absolute physiologic signal values uplink telemetered from the implantable physiologic monitor. In the present invention, the relative physiologic signals are already derived and stored so that there is no need to make the time comparisons and correlate two sets of data from the implantable medical device and the externally worn sensor module either manually or using a further correlation device. The present invention is particularly advantageously employed to adjust the absolute pressure values derived from the implantable blood pressure sensor and stored in the implantable monitor.

In the context of the implantable therapy delivery device, the present invention advantageously derives the relative physiologic signal values that more accurately reflect the state or condition of the body organ or part to be treated by the therapy. In the case of a cardiac therapy device dependent on cardiac blood pressure, the relative blood pressure values more accurately reflect cardiac output and are more reliably usable than absolute blood pressure values which can change substantially with changes in weather and elevation of the patient.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS OF THE INVENTION

Figure 1:
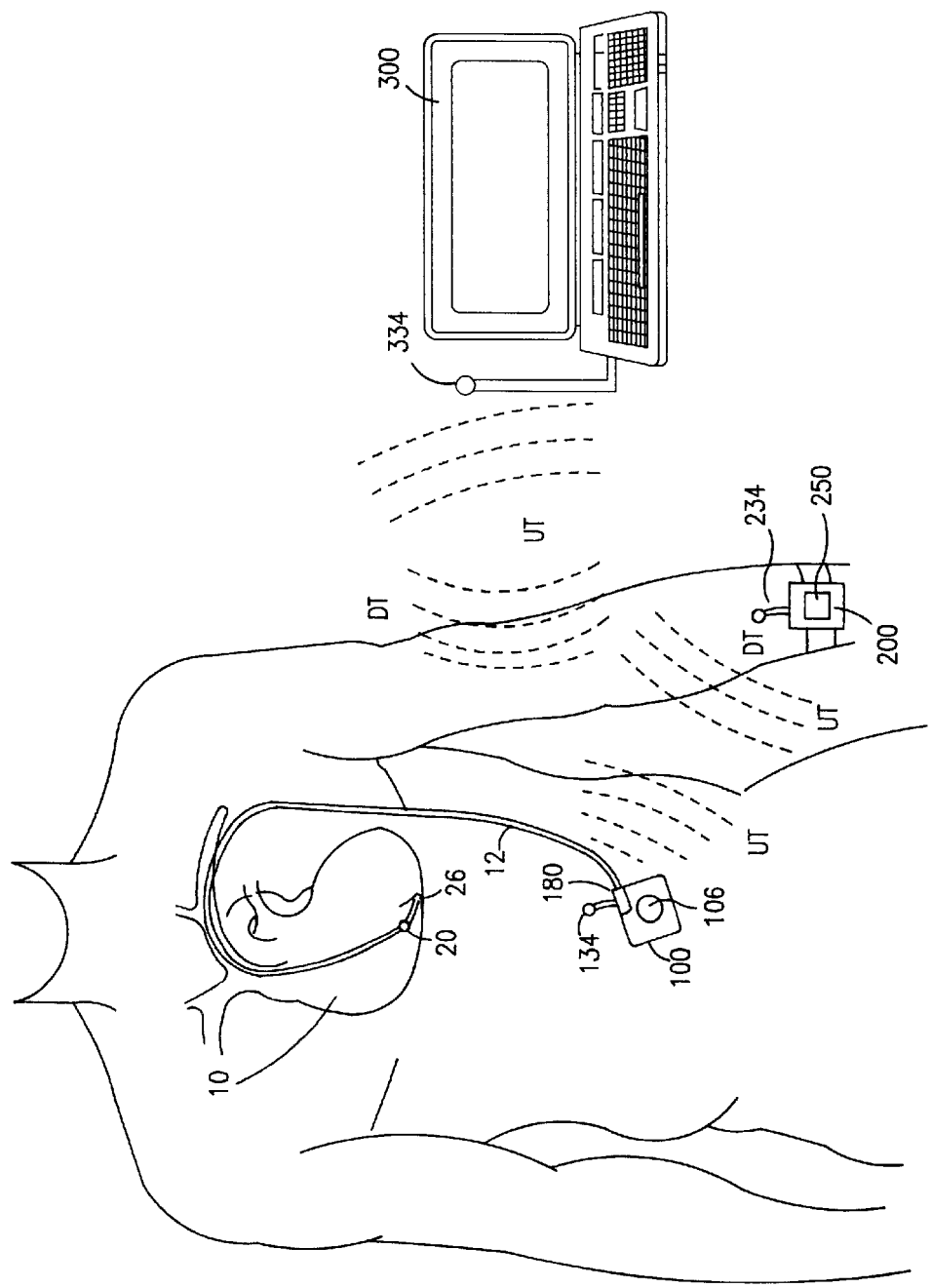
FIG. 1 is a schematic illustration of the telemetry communication between an implantable medical device and physiologic sensor and both a patient worn sensor module or external monitoring device and an external monitor/programmer employed in the present invention in accordance with the method illustrated in FIG. 5.
Figure 5:
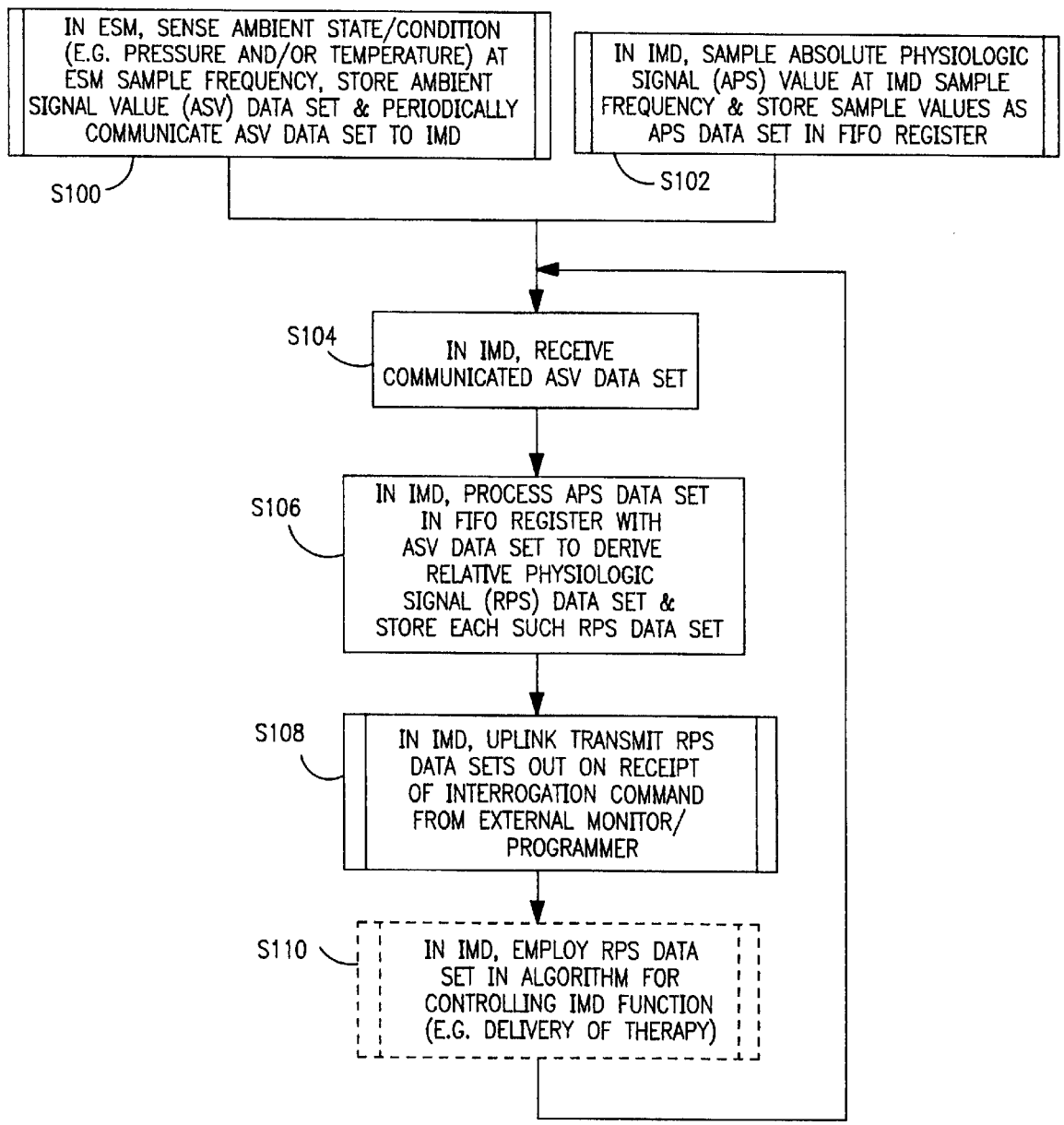
FIG. 5 is a simplified flow chart setting forth the steps of one preferred method of the present invention usable in the system of FIGS. 1–4.

FIG. 1 schematically illustrates the relation and telemetry communication between an implantable medical device 100 and physiologic sensor 20 and both first and second external monitoring devices, namely an external monitoring device or patient worn sensor module 200 and an external monitor or programmer 300, employed in the present invention in accordance with the method illustrated in FIG. 5. The implantable medical device 100 is depicted implanted in the abdomen of the patient, and it is coupled at its connector 180 to a lead 12 extending through blood vessels into the right ventricle of the patient's heart 10. It will be understood from FIG. 3 that when the implantable medical device 100 includes a cardiac therapy delivery device or function, that additional leads or catheters used in the delivery of the particular therapy extend from the implantable medical device 100 to the heart 10.

The physiologic sensor 20 is located on lead 12 just proximal to a lead distal tip fixation mechanism 26 for fixing the physiologic sensor 20 in position despite continuous movement of the heart 10. The physiologic sensor 20, lead 12 and attachment mechanism may take any of the known forms for sensing blood pressure, blood temperature, blood gas components, or the like. Preferably, however, the lead 12 and physiologic sensor 20 correspond to those disclosed in detail in the above-incorporated, commonly assigned, '434 and '752 patents for deriving absolute blood pressure and temperature signals.

Figure 2:
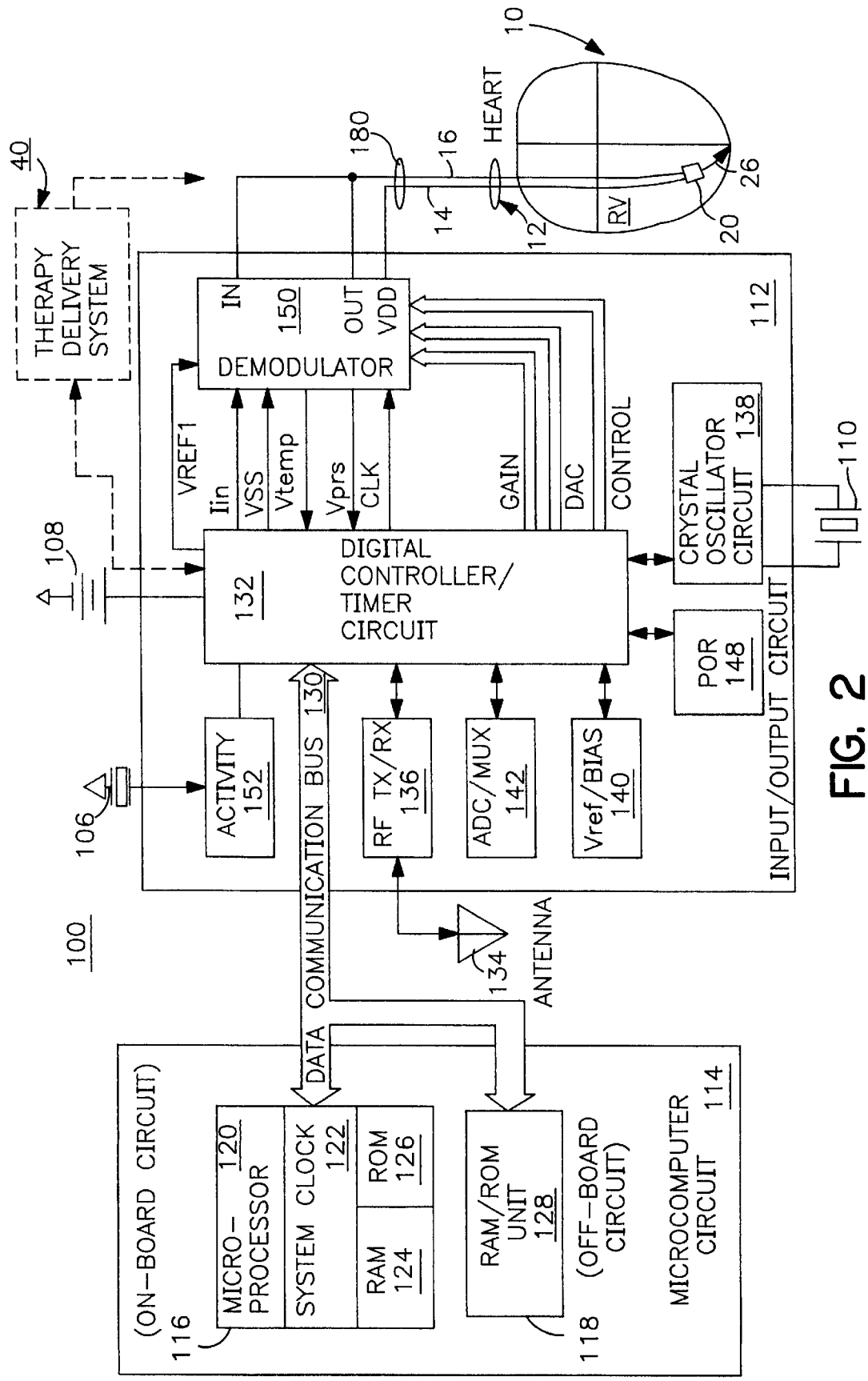
FIG. 2 is block diagram of an implantable medical device and lead system of FIG. 1 and specifically an implantable, programmable blood pressure and temperature Dmonitor usable alone or as part of a therapy delivery device and lead system.

The implantable medical device 100 is also depicted as optionally including an activity sensor 106 that is coupled to an activity signal processing circuit as shown in FIG. 2 and described further below.

An RF telemetry antenna 134 is depicted schematically in FIG. 1 extending from the connector 180 of the implantable medical device 100. The RF telemetry system preferably operates at a long range of about 2 meters or more in a relatively high frequency range. The long range RF telemetry antenna 134 and telemetry system may take any of the forms described for example, in the above-incorporated '869 patent and '624 patent application. The present invention may be practiced using any of the above referenced telemetry transmission systems including the transmission of RF telemetry signals or the equivalent transmission of signals using the body as a coupling medium for both electrical signals and acoustic signals as set forth in the above-incorporated '773, '950, '897, and '859 patents. For convenience of description, the preferred embodiment is described as follows using long range RF telemetry transmission, but the invention and following claims are not be interpreted as so limited. Similarly, the terms "telemeter", "telemetry transmission" and the like are intended to embrace any such action and manner of conveying data and commands between the implantable medical device and external monitoring devices or programmers.

A wrist worn external physiologic sensor module 200 having an RF telemetry antenna 234 delivering a downlink RF telemetry transmission DT to the implantable medical device RF telemetry antenna 134 is also schematically illustrated in FIG. 1. Ambient conditions that affect the sensed physiologic signal values, e.g. barometric pressure for blood pressure and ambient temperature or blood temperature elevated by a fever, are monitored in the externally worn sensor module 200. The ambient signal values are periodically transmitted by a transceiver in the externally worn sensor module 200 in the downlink RF telemetry transmission DT to the implantable medical device telemetry transceiver for use in the processing of the sensed absolute physiologic signal values to derive relative physiologic signal values., e.g. relative pressure and temperature.

The external monitoring device or sensor module 200 may also periodically transmit a time synchronization signal to the implantable medical device 100 to reset its real time clock and synchronize it with the real time clock of the external sensor module 200. This feature ensures that the sampled absolute physiologic signal values are time correlated accurately with the ambient signal values that are transmitted from the external sensor module 200. The time synchronization signal may be transmitted independently of or accompany the downlink RF transmission of the ambient signal values.

In the context of an implantable physiologic monitor, the relative and, optionally, the absolute and/or ambient physiologic signal values are stored in memory for telemetry out to an external programmer 300 in an uplink RF telemetry transmission UT initiated by medical personnel operating the external programmer 300. In the case where the implantable medical device is an implantable therapy delivery device, the relative physiologic signal values are also employed in therapy delivery algorithms to control the delivery of the therapy. The present invention is preferably implemented in a system as depicted in FIG. 1 operating in accordance with the flow chart of FIG. 5 to deliver a therapy and/or monitor a physiologic condition comprising relative blood pressure and/or temperature as described as follows. However, the principles of the present invention are applicable to the derivation of other relative physiologic signals.

FIG. 2 is a simplified block diagram of the pressure sensing lead 12 and implantable medical device 100 in relation to patient's heart 10. The lead 12 has first and second lead conductors 14 and 16 extending from the connector 180 to the physiologic sensor 20 disposed near the distal fixation mechanism 26. The physiologic sensor 20 preferably includes a variable pickoff capacitor and a fixed reference capacitor and signal modulating circuit described in detail in the above-incorporated, commonly assigned, '434 and '752 patents which develops both blood pressure and temperature time-modulated intervals that are decoded as blood pressure and temperature signal values in demodulator 150. The proximal end of lead 12 is formed as a conventional bipolar, in-line pacing lead connector and is coupled to the monitor connector 180 which is formed as a conventional bipolar in-line pacemaker pulse generator connector block assembly.

Crystal oscillator circuit 138 and crystal 110 provide the basic timing clock for the digital controller/timer circuit 132. Vref/BIAS circuit 140 generates stable voltage reference Vref and current levels from battery 108 for the circuits within the digital controller/timer circuit 132, and the other identified circuits including microcomputer 114 and demodulator 150. Power-on-reset circuit 148 responds to initial connection of the circuitry to the battery 108 for defining an initial operating condition and also resets the operating condition in response to detection of a low battery voltage condition. Analog-to-digital converter (ADC) and multiplexor circuit 142 digitizes analog signals Vprs and Vtemp received by digital controller/timer circuit 132 from demodulator 150 for storage by microcomputer 114.

Data signals transmitted out through RF transmitter/receiver circuit 136 during telemetry are multiplexed by ADC/MUX circuit 142. Voltage reference and bias circuit 140, ADC/MUX circuit 142, POR circuit 148, crystal oscillator circuit 138 and optional activity circuit 152 may correspond to any of those presently used in currently marketed, implantable cardiac pacemakers.

The digital controller/timer circuit 132 includes a set of timers and associated logic circuits connected with the microcomputer 114 through the data communications bus 130. Microcomputer 114 contains an on-board chip including microprocessor 120, associated system clock 122, and on-board RAM and ROM chips 124 and 126, respectively. In addition, microcomputer 114 includes an off-board circuit 118 including separate RAM/ROM chip 128 to provide additional memory capacity. Microprocessor 120 is interrupt driven, operating in a reduced power consumption mode normally, and awakened in response to defined interrupt events, which may include the periodic timing out of data sampling intervals for storage of monitored data, the transfer of triggering and data signals on the bus 130 and the receipt of programming signals. A real-time clock and calendar function may also be included to correlate stored data to time and date.

In a fuirther variation, provision may be made for the patient to initiate storage of the monitored data through an external programmer or a reed switch closure when an unusual event or symptom is experienced. The monitored data may be related to an event marker on later telemetry out and examination by the physician.

Microcomputer 114 controls the operating functions of digital controller/timer 132, specifying which timing intervals are employed, and controlling the duration of the various timing intervals, via the bus 130. The specific current operating modes and interval values are programmable. The programmed-in parameter values and operating modes are received through the antenna 134, demodulated in the RF transmitter/receiver circuit 136 and stored in RAM/ROM chip 128.

Data transmission to and from the external programmer 300 of FIG. 1 is accomplished by means of the telemetry antenna 134 and the associated RF transmitter and receiver 136, which serves both to demodulate received downlink RF telemetry transmission DT and to transmit uplink RF telemetry transmission UT. A number of power, timing and control signals described in greater detail in the above-incorporated, commonly assigned, '434 and '752 patents are supplied by the digital controller/timer circuit 132 to the demodulator 150 to initiate and power the operation of the physiologic sensor 20 and selectively read out the pressure and temperature signals Vprs and Vtemp. An active lead conductor 16 is attached through the connector block terminals to input and output terminals of demodulator 150 which supplies a voltage VREG at the output terminal. A passive lead conductor 14 is coupled through to the VDD supply terminal of the demodulator 150. The voltage signals Vprs and Vtemp developed from intervals between current pulses received at the input terminal are provided by demodulator 150 to the digital controller/timer circuit 132. The voltage signals Vprs and Vtemp are converted to binary data in an ADC/MUX circuit 142 and stored in RAM/ROM chip 128 in a manner well known in the art.

As configured in solid lines in FIG. 2, the implantable medical device 100 functions as an implantable physiologic signal sensor, specifically for monitoring and storing blood pressure and temperature from an absolute pressure and temperature sensor and optionally the patient activity and EGM as described below. FIG. 2 also shows the configuration of a therapy delivery device by inclusion of the therapy delivery system block 40 shown in broken lines. The particular therapy delivery system 40 may include one or more of the systems depicted in FIG. 3 as described below.

As depicted in FIGS. 1 and 2, the implantable medical device 100 periodically stores digitized data related to blood pressure and/or temperature and optionally stores digital data related to patient activity level, both optionally correlated to time and date when it is enabled to operate as an implantable heart monitor. The implantable medical device 100 may also optionally include a further lead connector for connection with further lead for implantation in a right heart chamber having an exposed unipolar distal electrode from which an electrogram (EGM) may be derived. The further lead may also have an oxygen or other blood gas sensor module, a pH sensor, or the like in the distal segment of the lead. A suitable oxygen sensor module bearing lead and oxygen sensor demodulator is disclosed in commonly assigned U.S. Pat. No. 4,750,495, incorporated herein by reference.

The modification of the implantable medical device 100 could also include a cardiac EGM sensing lead having sense electrodes located in a heart chamber or have sense electrodes separated apart on the device housing as in the MEDTRONIC® Reveal implantable heart monitor coupled with a sense amplifier within input/output circuit 112. In that optional configuration, the EGM signal may be employed to identify the onset of a cardiac depolarization in each heart cycle and automatically initiate either the monitoring and storage operations or simply initiate the storage of the data derived by continuous monitoring which would otherwise not be stored. Alternatively, the monitored parameters including patient activity, blood pressure and temperature, blood pH, blood oxygen or other gas saturation level and EGM can be continuously monitored.

In any monitoring configuration, monitoring can be initiated and enabled by the patient when the patient feels the onset of a cardiac arrhythmia. In this case, the monitoring may be initiated by application of a magnet over the implantable medical device 100 to close a reed switch or magnetic sensor (not shown). Alternatively, the wrist worn sensor module 200 may be supplied with a switch that may be closed by the patient to send a monitoring command to the implantable medical device 100 via a downlink RF telemetry transmission DT to enable the monitoring function for a pre-set period.

Referring again to the specific embodiment of FIG. 2, patient activity, blood pressure and blood temperature are capable of being monitored when monitoring is enabled by any of these means. The absolute blood pressure and temperature signals are preferably sensed about once every second or few seconds which may be related to the cardiac cycle, typical patient respiration rates, or the like, and digitized and stored in RAM registers allocated thereto on a FIFO basis. The sampled and stored blood pressure and temperature data are absolute pressure and temperature values that do not account for barometric pressure or ambient temperature affecting the ambient pressure and temperature load on the physiologic (pressure and temperature) sensor 20.

In accordance with one embodiment of the present invention, the ambient signal values are periodically transmitted by a transceiver in the externally worn sensor module 200 in downlink RF telemetry transmissions DT to the implantable medical device telemetry transceiver 136 for deriving the relative physiologic signal values from the data set of absolute physiologic signal values already stored in RAM/ROM chip 128 on a FIFO basis. It will be understood that the present invention contemplates that the downlink RF telemetry transmissions of at least one but preferably a set of the ambient signal values sensed at the same frequency as the absolute physiologic signal values and stored as an ambient signal data set in memory in the sensor module 200. The frequency of downlink RF telemetry transmissions can be adjusted to recur at a frequency that fits the circumstances of the particular patient, the particular physiologic condition or state being monitored or the physiologic sensor. In this way, the relative physiologic signal values are derived on a timely basis that is useful for monitoring or controlling therapy delivery.

However, as noted above, downlink RF telemetry transmissions to and uplink RF telemetry transmissions from the implantable medical device 100 consume battery power as the receiver and transmitter, respectively, are powered up. The implantable medical device 100 typically samples physiologic signals on a relatively frequent basis either to gather data or to control therapy delivery in a timely manner, and this normal primary activity consumes battery power. The frequency of downlink RF telemetry transmissions is preferably minimized, while retaining the ability to meaningfully employ the ambient signal value or ambient data set, in order to minimize the additional consumption of battery power in the implantable medical device 100 while practicing the present invention.

In the context of an implantable medical monitoring system, the absolute physiologic signals and the corresponding ambient signals are preferably derived at a programmable sampling frequency and stored in memory in the implantable medical device 100 and in the external sensor module 200. The periodic downlink RF telemetry transmissions DT may be set to recur at a rate of once every 1–10 minutes, for example, so that energy consumption from the implanted medical device battery 108 in receiving and processing the downlink RF telemetry transmissions DT is minimized.

Each time that the ambient signal data set is received, each ambient signal value in the transmitted data set is combined with a corresponding (in time based location in the data set) stored absolute physiologic signal value in the stored data set to derive the relative physiologic data set. The relative physiologic data set is then stored in device memory allocated to the storage of the most recent, retrospective, data set on a FIFO basis. The stored relative physiologic data sets are read out and conveyed via uplink RF telemetry to the external programmer 300 at the point in time when a medical attendant initiates a downlink RF telemetry transmission of an interrogation command to the implantable medical device 100. In this case, a date and time stamp may be appended to each stored relative physiologic signal data set for uplink RF telemetry with it.

If the external monitoring device fails to operate and downlink RF telemeter the ambient signal value for some reason, e.g., depletion of its battery or failure of the external ambient sensor or removal from the patient to a location outside the RF telemetry range, the FIFO register holding the absolute physiologic data set will fill. At that point, the oldest data will be lost and no further relative physiologic data will be derived and stored. Alternatively, the absolute physiologic data set can be stored with a notation identifying it until the implantable medical device memory is interrogated by a medical attendant.

Moreover, the sensor module 200 can uplink RF telemetry transmit a request to the externally worn sensor module 200 to downlink RF telemeter an updated ambient signal value. For example, the request may be transmitted if the implantable medical device 100 fails to receive an updated ambient signal value within a certain time period from receipt of a preceding ambient signal value or data set. In addition, the external sensor module 200 can alert the patient that its battery requires replacement or that its sensor is not working for some reason or another.

In a further variation, the communication of ambient signal values to the implanted medical device may be triggered by the patient rather than being triggered on a continuous basis. The ambient signal values are continuously obtained and stored in sensor module memory registers on a FIFO basis. Similarly, the absolute physiologic signal values are obtained and stored in implantable medical device memory registers on a FIFO basis. The patient can close a switch on the patient worn sensor module 200 to initiate a downlink RF telemetry transmission of an ambient signal data set when an unusual event or symptom is experienced. The downlink RF telemetry transmitted ambient signal data set is combined with the absolute physiologic data set to derive and store the relative physiologic data set as described above. The downlink RF telemetry transmissions of the ambient signal data set and the derivation of relative physiologic signal data can continue for a preset time period. A date and time event marker is stored with the relative physiologic data set, and the data set is retained for later telemetry out to the external programmer 300 and examination by the physician or other medical attendant.

Finally, the external sensor module can be programmed to initiate a downlink RF telemetry transmission of an updated ambient signal value data set when certain events occur. The sensor module 200 is capable of comparing successively sensed ambient signal values that it is storing as a data set for transmission at the preset time to the implantable medical device 100. The sensor module determines as a result of the comparison when a change occurs in the ambient state or condition being monitored that is significant enough that it will affect the absolute physiologic signal being measured by the implantable medical device. The sensor module itself can then initiate a transmission of the current ambient signal value or data set.

Figure 3:
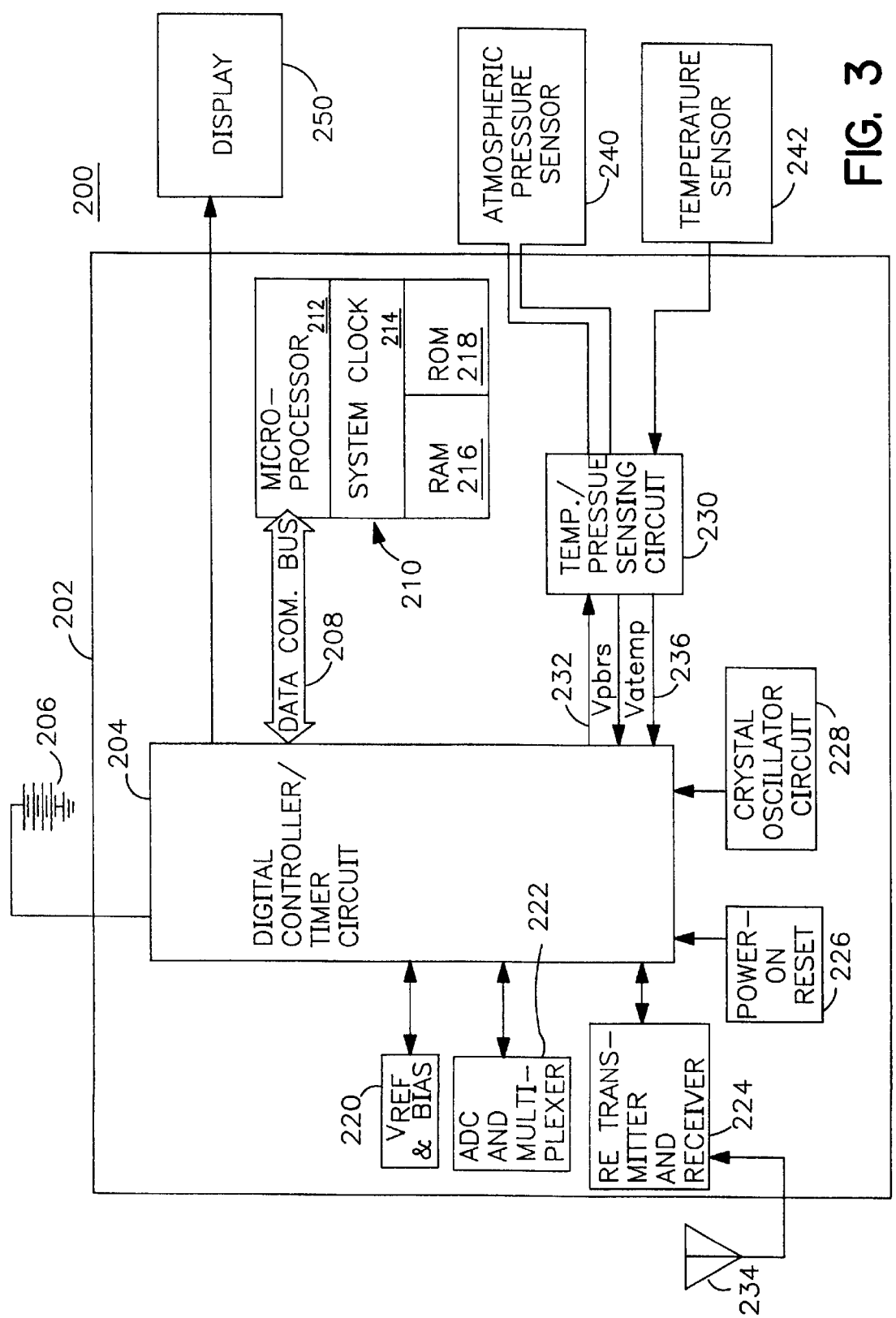
FIG. 3 is an expanded block diagram of exemplary cardiac therapy delivery apparatus usable in conjunction with the implantable, programmable blood pressure and temperature monitor of FIGS. 1 and 2.

In the context of an implantable cardiac therapy delivery device, the relative physiologic signal values, namely the relative blood pressure and/or temperature signal values are used in an operating algorithm stored in RAM/ROM chip 128 to control the delivery of the therapy. A therapy delivery system 40 is schematically illustrated In FIG. 2, and exemplary cardiac therapy delivery apparatus usable in conjunction with the implantable, programmable blood pressure and temperature monitor of FIGS. 1 and 2 are illustrated in FIG. 3. The implantable medical device 100 may be configured to operate an implantable heart assist device or pump 40a implanted in patients awaiting a heart transplant operation. In this case, the derived relative blood pressure and/or temperature values may be used to modulate the action of the pump to maintain adequate cardiac output. Or it may be configured to include any one or a combination of the anti-tachycardia pacer 40b, anti-bradycardia pacer 40c, cardioverting apparatus 40d and/or defibrillating apparatus 40e having suitable leads and electrodes extending from the implantable therapy delivery medical device 100 to the patient's heart 10 for sensing the EGM and delivering pacing pulses or cardioversion/defibrillation shocks. In these cases, the derived relative blood pressure and/or temperature values may be used to modulate the pacing rate to maintain adequate cardiac output or to augment the detection of malignant tachyarrythmias and fibrillation or flutter. Or the implantable medical device may be configured as a MEDTRONIC® Transform™ Cardiomyostimulator 40g having suitable leads extending to the patient's heart and the skeletal muscle wrapped about the heart to sense the cardiac EGM and time delivery of the muscle stimulation pulses. Again, the derived relative blood pressure and/or temperature values may be used to modulate the muscle stimulation rate to maintain adequate cardiac output. Alternatively, the implantable medical device 100 may be configured to include the drug delivery apparatus 40f which is coupled to a suitable catheter extending to the patient's heart 10 or vascular system to directly deliver drugs to treat hypertension, for example. In each case, a programmable operating algorithm governs the operation of the device and the control of the delivery of the therapy as a function of the relative physiologic signal value, e.g. relative blood pressure and/or blood temperature. As suggested in the above-incorporated '505, '859, and '987 patents, these therapy delivery apparatus 40a–40g may be combined in various combinations as necessary to treat a given patient.

Figure 4:
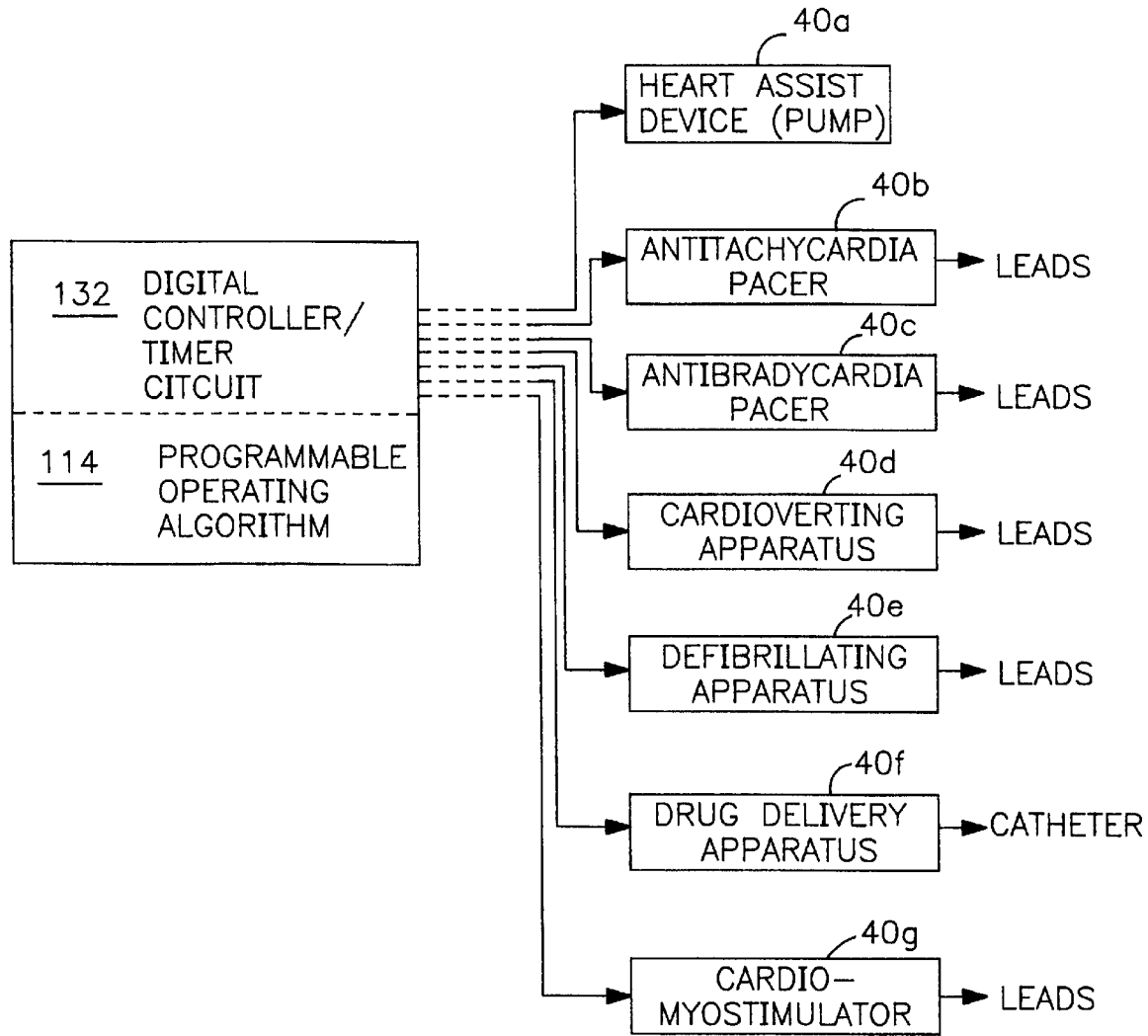
FIG. 4 is a block diagram of the patient worn sensor module or external monitoring device for sensing the ambient signal value, specifically barometric pressure and/or temperature, and for downlink telemetering the sensed ambient signal value to the implantable medical device of FIGS. 1 and 2.

FIG. 4 is a block diagram of the patient worn sensor module 200 for sensing the ambient signal value, specifically barometric pressure and/or ambient or patient systemic temperature, and for downlink RF telemetering the sensed ambient signal value to the implantable medical device of FIGS. 1–3. The sensor module 200 can be worn about the patient's wrist and include the electronic operating system 202, a battery 206, an atmospheric pressure sensor 240, a temperature sensor 242, an RF telemetry antenna 234 and optionally may include a wrist watch function and display 250 and operating buttons (not shown).

The electronic operating system 202 includes the digital controller/timer circuit 204 and the associated components including the microcomputer 210, Vref/BIAS circuit 220, ADCGMUX circuit 222, RF transmitter/receiver circuit 224, power-on-reset (POR) circuit 226, crystal oscillator 228, ambient temperature and/or barometric pressure sensing circuit 230 coupled to the atmospheric pressure sensor 240 and the ambient temperature sensor 242. Crystal oscillator 228 provides the basic timing clock for the digital controller/timer circuit 204. Vref/BIAS circuit 220 generates stable voltage reference Vref and current levels from battery 206 for the circuits within the digital controller/timer circuit 204 and the other identified circuits and microcomputer 210. Power-on-reset circuit 226 responds to initial connection of the circuitry to the battery 206 for defining an initial operating condition and also resets the operating condition in response to detection of a low battery voltage condition. Analog-to-digital converter (ADC) and multiplexor (MUX) circuit 222 digitizes analog signals Vbprs and/or Vatemp received by digital controller/timer circuit 132 from temperature/pressure sensing circuit 230 for temporary storage in RAM chip 216 by microcomputer 210 and for telemetry out as a ambient sensor value data set in a downlink RF telemetry transmission. The stored set of ambient signal values in the data set transmitted out through RF transmitter/receiver circuit 224 during telemetry are multiplexed by ADC/MUX circuit 222.

The digital controller/timer circuit 204 includes a set of timers and associated logic circuits connected with the microcomputer 210 through the data communications bus 208. Microcomputer 210 contains an on-board chip including microprocessor 212, associated system clock 214, and on-board RAM and ROM chips 216 and 218, respectively. Microcomputer 210 also controls the operating functions of digital controller/timer 204 and display 250, specifying which timing intervals are employed, and controlling the duration of the various timing intervals, via the bus 208. The specific current operating modes and interval values are programmable using instructions telemetered from the programmer 300. The programmed-in parameter values and operating modes are received through the antenna 234, demodulated in the RF transmitter/receiver circuit 224 and stored in RAM chip 216.

Microprocessor 210 is interrupt driven, operating in a reduced power consumption mode normally, and awakened in response to defined interrupt events. One defined interrupt event is the periodic timing out, e.g. every 10 minutes, of a programmable sampling timer that results in an instruction to the digital controller/timer circuit 204 to provide trigger signals on sample line 232 to sample the ambient atmospheric pressure signal Vbprs and/or temperature signal Vatemp from temperature/pressure sensing circuit 230. Then, the ambient atmospheric pressure signal Vbprs and/or temperature signal Vatemp is/are encoded for downlink RF telemetry transmission DT to the implanted medical device 100. The downlink RF telemetry transmission DT of the encoded ambient signal values to the implantable medical device 100 is conducted employing the transceiver 224 and RF telemetry antenna 234. The downlink RF telemetry transmission DT is received by RF antenna 134 and transceiver 136, the ambient pressure and/or temperature sense signal values in the transmitted data set are decoded, and the decoded signal values are stored and employed in the implantable medical device.

The patient worn sensor module 200 may also receive instructions or requests in uplink RF telemetry transmissions from the implantable medical device 100 as well as from the external programmer 300 of FIG. 1. Such telemetry transmission and reception is accomplished by means of the telemetry antenna 234 and the associated RF transmitter and receiver 224, which serves both to demodulate received uplink RF telemetry transmissions from implantable medical device 100 and to transmit the depicted downlink RF telemetry transmission DT.

The sensor module 200 may also periodically transmit a time synchronization signal to the implantable medical device 100 to reset its real time clock and synchronize it with the real time clock of the sensor module 200. This feature ensures that the sampled absolute physiologic signal values are time correlated accurately with the ambient signal values that are transmitted from the external sensor module 200. The time synchronization signal may transmitted independently of or accompany the downlink RF transmission of the ambient signal values.

FIG. 5 is a simplified flow chart setting forth the steps of a preferred embodiment of the method of the present invention usable in the system of FIGS. 1–4. Preferably, as described above, the downlink RF telemetry transmission of the ambient signal values or data sets is initiated by the externally worn sensor module 200 on a fixed periodic basis which is independent of the sampling frequency of the implantable medical device 100. The received ambient signal values are used in the derivation of a set of relative physiologic signal value data from a set of absolute physiologic signal values previously stored in implantable medical device memory registers on a FIFO basis in the period between successive downlink RF telemetry transmissions of the ambient signal values. The relative physiologic signal data set is then stored in implantable device memory. One or more sets of such relative physiologic data may be retained in implantable device memory, depending on memory capacity. The stored relative physiologic signal data sets are replaced by subsequently derived relative physiologic signal data sets on a FIFO basis if the memory becomes filled before the accumulated data sets are uplink communicated to an external medical device receiver.

The stored relative physiologic signal data set(s) remain in implantable device memory in the event that the implantable medical device 100 fails to receive an updated ambient signal value via downlink RF telemetry from the externally worn sensor module 200. A date and time tag may be stored in implantable device memory with the stored relative physiologic signal data set(s) for later RF telemetry out to the external programmer 300 so that the physician can ascertain when the data set(s) was stored. In the context of implantable therapy delivery devices, the therapy delivery algorithm may revert to a default mode in the event that an ambient signal value is not received within a predetermined time interval and becomes aged.

In steps S100 and S102 of FIG. 5, assuming that the monitoring function is enabled in the implantable medical device 100, both the implantable medical device (IMD) 100 and the patient worn sensor module 200 (EMD) are independently monitoring the physiologic conditions or states of interest, e.g., the absolute blood pressure and temperature and the barometric pressure and ambient temperature, respectively. Preferably, they monitor and derive sets of ambient signal values and absolute physiologic signal values at the same frequency. In step S100, the external sensor module (ESM) 200 times out its downlink telemetry transmission period or is triggered by the patient or BY a command received in an uplink RF telemetry transmission from the implantable medical device 100. In response to any of these events, the ESM then transmits the ambient signal data set of ambient signal values (e.g., barometric pressure and ambient temperature) affecting the measured physiologic state or condition, and transmits the encoded, digitized ambient signal value (ASV) data in a downlink RF telemetry transmission to the implantable medical device 100 (IMD).

At the same time and independently of the operations of the ESM in step S100, the IMD is monitoring the patient's physiologic condition or state (e.g., cardiac blood pressure or temperature) in step S102. In step S102, the IMD samples the absolute physiologic signal (APS) values and stores them as APS data in the IMD memory on a FIFO basis. As noted above the sampling rate and memory registers may be configured to retain APS data extending over a time period that is programmable and may exceed or be shorter than the period between successive downlink RF telemetry transmissions of the ASV data sets. preferably the APS and ASV data sets are the same in number and are collected at the same sampling frequency extending over the same time period.

In step S104, the downlink RF telemetry transmission of the ASV data set is received, and decoded. In step S106, the IME processes the APS data SET in the FIFO registers of the IMD memory with the received ASV data SET to derive the relative physiologic signal (RPS) data set. The RPS data set is then stored in IMD memory and retained under the conditions described above in the implantable medical device 100.

In step S108, the user of the external programmer 300 of FIG. 1 downlink RF telemeters an interrogation command to the IMD 100. The IMD 100 responds by encoding and transmitting the RPS data in an uplink RF telemetry transmission to the external programmer 300.

Optionally, if the implantable medical device 100 is configured as a cardiac therapy delivery device, then the RPS values in the RPS data set, e.g., the relative blood pressure and/or temperature signal values, are employed in the therapy delivery algorithm to control the delivery of the therapy in step S116.

Figure 6:
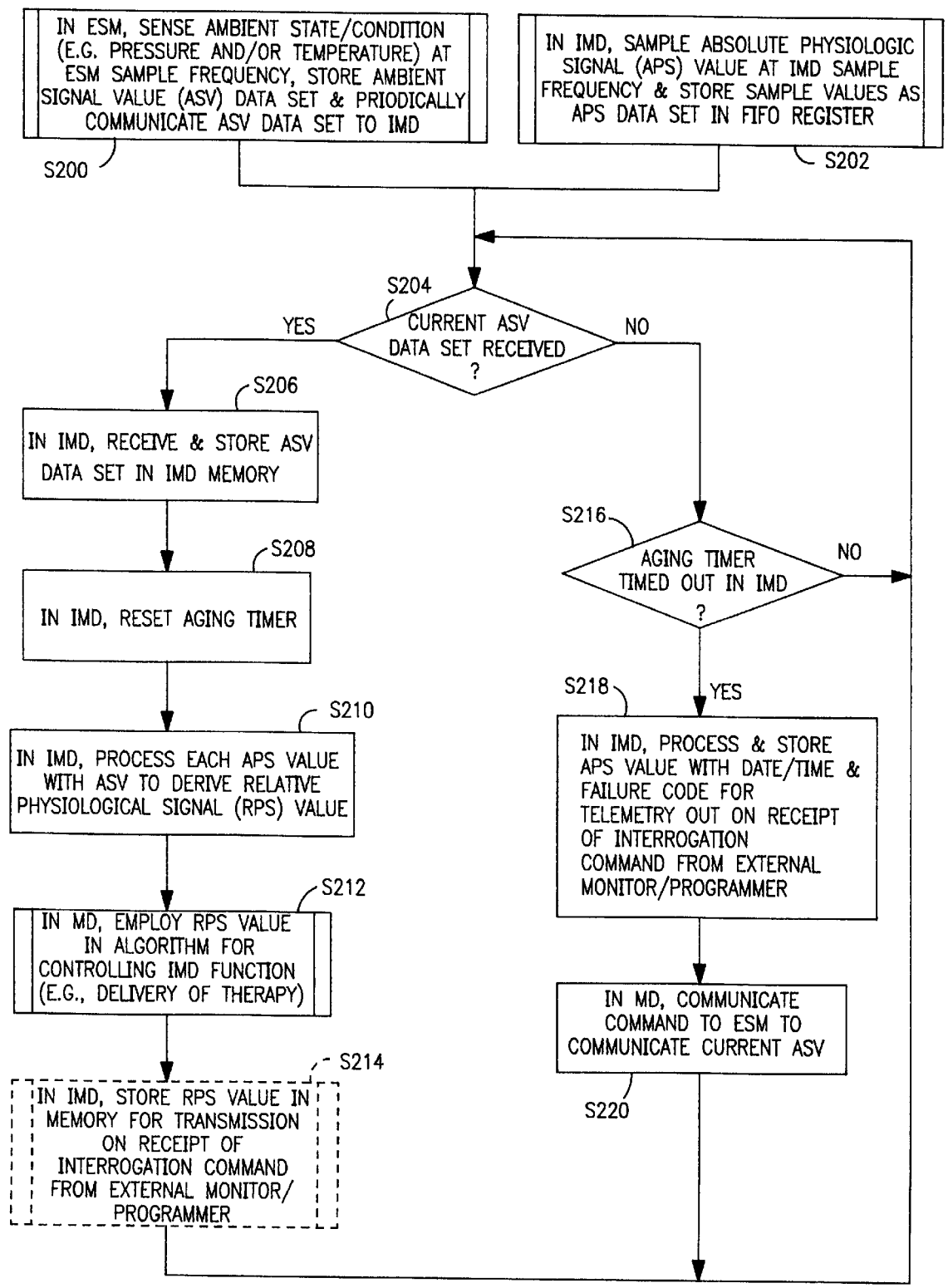
FIG. 6 is a simplified flow chart setting forth the steps of another preferred method of the present invention usable in the system of FIGS. 1–4.

FIG. 6 is a simplified flow chart setting forth the steps of another preferred method of the present invention usable in the system of FIGS. 1–4, particularly usable in a therapy delivery device where it is deemed possible to rely upon an earlier derived and transmitted ambient signal value at least for a certain programmable aging time period. In this method, one or more ASV is transmitted periodically from the ESM to the IMD, stored until the next ASV is received and used during that time period or until an aging timer times out to derive an RPS value each time an APS value is sensed by the IMD. The derived RPS values are used to control delivery of a therapy.

Steps S200 and S202 of FIG. 6 correspond generally to steps S100 and S102 described above. The IMD sample frequency in step S202 may be scaled to the patient's heart rate for detection of changes in cardiac blood pressure due to cardiac function during the heart cycle for either rate responsive pacing or for detection of a malignant tachyarrythmia or may be scaled to the patient's breathing rate for changes reflected onto the cardiac blood pressure due to respiration to determine patient activity level, for example. The IMD sample frequency of the APS values may be governed by other factors for use in the other implantable medical devices illustrated in FIG. 4. The same sample frequency may be used in step S200 for the ESM sample frequency.

The ESM frequency of transmission of the ASV related to barometric pressure may be the on the order of minutes in the expectation that the patient is unlikely to experience more rapid changes in barometric pressure or that any change in the interim will not place the patient at risk. However, as noted above, the ESM can be programmed to initiate a downlink telemetry transmission of an updated ASV data set when certain events occur. The ESM is capable of comparing successively sensed ASVs that it is storing as a data set for transmission at the preset time to the IMD. The ASM determines as a result of the comparison when a change occurs in the ambient state or condition being monitored that is significant enough that it will affect the APS being measured by the IMD. The ASM itself can then initiate a transmission of the current ASV or data set to the IMD before the transmission period elapses for use in processing the APS until the next transmission of an updated ASV.

In steps S204–S208, when a current ASV data set (which may be a single ASV) is received, it is stored in IMD memory and resets an aging timer that is timing out in the IMD. In step S210, the APS values that are received thereafter are processed to derive RPS values using the stored ASV data set until the next ASV data set is received or the aging timer times out, whichever occurs first. In step S212, the derived RPS value is used in the operating algorithm of the therapy delivery device to control the delivery of the therapy. In optional step S214, the RPS values are stored as RPS data sets for later transmission to the external programmer upon receipt of an interrogation command.

Returning to step S204, as long as a current ASV data set is not received in the IMD, the aging timer continues to time out. If it times out in step S216 before it is reset in step S208, then the derivation of the RPS values and the steps S210–S214 employing the RPS values are halted. In step S218, various failure data can be recorded for subsequent transmission to the external programmer upon receipt of an interrogation command so that the medical attendant can analyze the data and determine what happened. In step S220, the IMD can transmit a command to the ESM requesting transmission of an updated ASV data set.

It should be noted that this method of FIG. 6 could also be used in the monitoring context by simply eliminating step S212 and following step S214.

In the above methods and systems, the combination in steps S106 and S210 of the ASV data set or the most recent ASV with the previously stored APS data set or each subsequently derived APS value to derive the RPS data set or the RPS value, respectively, depends on the nature of the physiologic signal sensed and the ambient condition or state monitored. In the case where the APS data set or APS value is derived by a blood pressure sensor and signal processor and the barometric pressure is sensed and transmitted as the ASV data set or ASV, the ambient barometric pressure signal value is normalized and subtracted from a corresponding normalized absolute blood pressure value previously stored or subsequently measured, respectively. in the case where the APS data set or APS value is derived by a blood temperature sensor and signal processor and the patient's skin temperature is sensed and transmitted as the ambient signal value, the ASV data set or ASV, ambient temperature signal value is normalized and subtracted from a corresponding normalized absolute blood temperature value previously stored or subsequently measured, respectively.

The practice of the present invention in the context of an implantable physiologic monitor advantageously eliminates the need, in an external programmer, to make time based comparisons of the external ambient signal values stored in a patient worn sensor module with the absolute physiologic signal values uplink telemetered from the implantable physiologic monitor to the external programmer. In the present invention, the relative physiologic signals are already derived and stored so that there is no need to make the time comparisons and correlate two sets of data from the implantable medical device and the externally worn sensor module.

In the context of the implantable therapy delivery device, the present invention advantageously derives the relative physiologic signal values that more accurately reflect the state or condition of the body organ or part to be treated by the therapy.

While particular embodiments of the invention have been disclosed herein in detail, this has been done for the purposes of illustration only, and is not intended to limit the scope of the invention as defined in the claims which follow. It is to be understood that various substitutions, alterations, or modifications can be made to the disclosed embodiment without departing from the spirit and scope of the claims. For example, while particular implementations of certain microprocessor based sub-systems have been described above, it is to be understood that they may be implemented in custom integrated circuit technologies. The above described implementations are simply those presently preferred or contemplated by the inventor, and are not to be taken as limiting the present invention to the disclosed embodiments. It is therefore to be understood, that within the scope of the appended claims, the invention may be practiced otherwise than as specifically described without actually departing from the spirit and scope of the present invention.

I claim:

1. An implantable medical device method for deriving relative physiologic signal value data for use by and/or storage within an implantable medical device implanted within a patient's body comprising the steps of:

providing an external monitoring device associated with the patient, and in the external monitoring device, sensing an ambient state or condition outside the body affecting a sensed physiologic state or condition within the body;

deriving an ambient signal value from the sensed ambient state or condition; and conveying the ambient signal value from the external monitoring device to the implantable medical device; and in the implantable medical device implanted in the patient's body, sensing a physiologic state or condition within the body of the patient;

deriving an absolute physiologic signal value from the sensed physiologic state or condition;

receiving the ambient signal value conveyed from the external monitoring device; and combining the derived absolute physiologic signal value and the conveyed ambient signal value to derive a relative physiologic signal value therefrom.

2. The method of claim 1, wherein the implantable medical device comprises implantable device memory and further comprising the step of:

storing a plurality of relative physiologic signal values as relative physiologic signal value data in the implantable medical device memory.

3. The method of claim 1, wherein the implantable medical device comprises an implantable monitor having implantable device memory and further comprising the step of:

storing a plurality of relative physiologic signal values as relative physiologic signal value data in the implantable medical device memory.

4. The method of claim 1, wherein the implantable medical device comprises an implantable monitor having implantable device memory and data conveying means for conveying data stored in the implantable memory to an external memory device further comprising the steps of:

storing a plurality of relative physiologic signal values as relative physiologic signal value data in the implantable medical device memory; and activating said data conveying means to convey the relative physiological signal value data stored in the implantable memory to an external medical device.

5. The method of claim 1, wherein the implantable medical device comprises implantable device memory and a therapy delivery system for delivering a therapy to the patient and further comprising the steps of:

storing a predetermined number of relative physiologic signal values as relative physiologic signal value data in the implantable medical device memory; and employing the relative physiologic signal values to control the delivery of the therapy by the implantable medical device.

6. The method of claim 1, wherein the implantable medical device comprises a therapy delivery system for delivering a therapy to the patient and further comprising the step of:

controlling the delivery of the therapy by the implantable medical device as a function of the relative physiologic signal value.

7. The method of claim 6, wherein the implantable medical device comprises a bradycardia pacing therapy delivery system for delivering a pacing therapy to the patient to provide sufficient cardiac output for the patient's body, the physiologic state or condition reflects the cardiac output requirement of the patient's body, and the delivery controlling step further comprises the steps of:

employing the relative physiologic signal values to control the bradycardia pacing rate of the implantable medical device to satisfy the cardiac output requirement; and delivering pacing pulses to the heart at the controlled pacing rate.

8. The method of claim 6, wherein the implantable medical device comprises an anti-tachyarrythmia therapy delivery system for delivering an anti-tachyarrythmia therapy to the patient to convert a tachyarrythmia to a normal heart rhythm, the physiologic state or condition reflects normal heart rhythm or a tachyarrythmia of the heart, and the delivery controlling step further comprises the steps of:

employing the relative physiologic signal values to differentiate between normal heart rhythm and a tachyarrythmia of the heart; and delivering an anti-tachyarrythmia therapy to the heart to convert the tachyarrythmia to a normal heart rhythm.

9. The method of claim 6, wherein the implantable medical device comprises a drug delivery system for delivering a drug to the patient to treat an abnormal medical state or condition, and the delivery controlling step further comprises the steps of:
  employing the relative physiologic signal values to determine dosage of the drug to the patient; and
  delivering the drug to the patient.

10. The method of claim 6, wherein the implantable medical device comprises a heart pump for providing sufficient cardiac output for the patient's body, the physiologic state or condition reflects the cardiac output requirement of the patient's body, and the delivery controlling step fuirther comprises the step of:
  employing the relative physiologic signal values to control the operation of the heart pump to satisfy the cardiac output requirement.

11. The method of claim 6, wherein the implantable medical device comprises a cardiomyostimulation pacing therapy delivery system for pacing a skeletal muscle wrapped about the patient's heart to augment contraction of the heart muscle to provide sufficient cardiac output for the patient's body, the physiologic state or condition reflects the cardiac output requirement of the patient's body, and the delivery controlling step fuirther comprises the steps of:
  employing the relative physiologic signal values to control the pacing of the skeletal muscle to satisfy the cardiac output requirement; and
  delivering pacing pulses to the skeletal muscle.

12. The method of any of the preceding claims 1–11, wherein the physiologic state or condition comprises the blood pressure of the patient, the sensed absolute physiologic signal value is absolute blood pressure value, the ambient state or condition comprises barometric pressure affecting the patient and the absolute pressure value, the relative physiologic signal value is relative blood pressure; and the step of combining the derived absolute physiologic signal value and the conveyed ambient signal value comprises subtracting the barometric pressure from the absolute blood pressure.

13. The method of any of the preceding claims 1–11, wherein the physiologic state or condition comprises the blood temperature of the patient, the sensed absolute physiologic signal value is absolute blood temperature, the ambient state or condition comprises systemic patient temperature affected by fever or ambient conditions, the relative physiologic signal value is relative blood temperature; and the step of combining the derived absolute physiologic signal value and the conveyed ambient signal value comprises subtracting the ambient temperature from the absolute blood temperature.

14. The method of any of the claims 1–11, wherein the steps performed by the external monitoring device are performed periodically to periodically derive and convey the ambient signal value to the implantable medical device, and the conveyed ambient signal value is used in the derivation of a plurality of relative physiologic signal values in the period between successive conveyances of the ambient signal value to the implantable medical device.

15. A system for deriving relative physiologic signal values from absolute physiologic signal values for use by and/or storage within an implantable medical device comprising:
  an external monitoring device associated with the patient comprising,
    external sensing means for sensing an ambient state or condition outside the body affecting a sensed physiologic state or condition within the body;
    signal processing means coupled with said external sensing means for deriving an ambient signal value from the sensed ambient state or condition; and
    signal conveying means for conveying the ambient signal value from the external monitoring device to the implantable medical device; and
  the implantable medical device implanted within a patient's body comprising,
    implantable sensing means for sensing a physiologic state or condition within the body of the patient;
    signal processing means coupled with said implantable sensing means for deriving an absolute physiologic signal value from the sensed physiologic state or condition;
    receiving means for receiving ambient signal values conveyed from said signal conveying means; and
    means for combining each derived absolute physiologic signal value and the sensed ambient signal value to derive a relative physiologic signal value therefrom.

16. The system of claim 15, wherein the implantable medical device further comprises:
  implantable device memory; and
  means for storing a plurality of relative physiologic signal values as relative physiologic signal value data in the implantable medical device memory.

17. The system of claim 15, wherein the implantable medical device comprises an implantable monitor further comprising:
  implantable device memory; and
  means for storing a plurality of relative physiologic signal values as relative physiologic signal value data in the implantable medical device memory.

18. The system of claim 15, wherein the implantable medical device comprises an implantable monitor further comprising:
  implantable device memory;
  means for storing a plurality of relative physiologic signal values as relative physiologic signal value data in the implantable medical device memory;
  data conveying means for conveying data stored in the implantable memory to an external memory device; and
  means for activating said data conveying means to convey the relative physiological signal value data stored in the implantable memory to said external medical device.

19. The system of claim 15, wherein the implantable medical device further comprises a therapy delivery system for delivering a therapy to the patient further comprising:
  implantable device memory;
  means for storing a predetermined number of relative physiologic signal values as relative physiologic signal value data in the implantable medical device memory; and
  means for employing the relative physiologic signal values to control the delivery of the therapy by the implantable medical device.

20. The system of claim 15, wherein the implantable medical device comprises a therapy delivery system for delivering a therapy to the patient further comprising:
  means for controlling the delivery of the therapy by the implantable medical device as a function of the relative physiologic signal value.

21. The system of claim 20, wherein the implantable medical device comprises a bradycardia pacing therapy delivery system for delivering a pacing therapy to the patient to provide sufficient cardiac output for the patient's body, the physiologic state or condition reflects the cardiac output requirement of the patient's body, and the delivery controlling means further comprises:
   means for employing the relative physiologic signal values to control the bradycardia pacing rate of the implantable medical device to satisfy the cardiac output requirement; and
   means for delivering pacing pulses to the heart at the controlled pacing rate.

22. The system of claim 20, wherein the implantable medical device comprises an anti-tachyarrythmia therapy delivery system for delivering an anti-tachyarytimia therapy to the patient to convert a tachyarrythmia to a normal heart rhythm, the physiologic state or condition reflects normal heart rhythm or a tachyarrythmia of the heart, and the delivery controlling means further comprises:
   means for employing the relative physiologic signal values to differentiate between normal heart rhythm and a tachyarrythmia of the heart; and
   means for delivering an anti-tachyarrythmia therapy to the heart to convert the tachyarrytlmia to a normal heart rhythm.

23. The system of claim 20, wherein the implantable medical device comprises a drug delivery system for delivering a drug to the patient to treat an abnormal medical state or condition, and the delivery controlling means further comprises:
   means for employing the relative physiologic signal values to determine dosage of the drug to the patient; and
   means for delivering the drug to the patient.

24. The system of claim 20, wherein the implantable medical device comprises a heart pump for providing sufficient cardiac output for the patient's body, the physiologic state or condition reflects the cardiac output requirement of the patient's body, and the delivery controlling means comprises:
   means for employing the relative physiologic signal values to control the operation of the heart pump to satisfy the cardiac output requirement.

25. The system of claim 20, wherein the implantable medical device comprises a cardiomyostimulation pacing therapy delivery system for pacing a skeletal muscle wrapped about the patient's heart to augment contraction of the heart muscle to provide sufficient cardiac output for the patient's body, the physiologic state or condition reflects the cardiac output requirement of the patient's body, and the delivery controlling means fiuther comprises:
   means for employing the relative physiologic signal values to control the pacing of the skeletal muscle to satisfy the cardiac output requirement; and
   means for delivering pacing pulses to the skeletal muscle.

26. The system of any of the preceding claims 15–25, wherein the physiologic state or condition comprises the blood pressure of the patient, the sensed absolute physiologic signal value is absolute blood pressure value, the ambient state or condition comprises barometric pressure affecting the patient and the absolute pressure value, the relative physiologic signal value is relative blood pressure; and the means for combining the derived absolute physiologic signal value and the conveyed ambient signal value comprises means for subtracting the barometric pressure from the absolute blood pressure to derive the relative blood pressure.

27. The system of any of the preceding claims 15–25, wherein the physiologic state or condition comprises the blood temperature of the patient, the sensed absolute physiologic signal value is absolute blood temperature, the ambient state or condition comprises systemic patient temperature affected by fever or ambient conditions, the relative physiologic signal value is relative blood temperature; and the means for combining the derived absolute physiologic signal value and the conveyed ambient signal value comprises means for subtracting the ambient temperature from the absolute blood temperature to derive the relative blood temperature.

28. The system of any of the preceding claims 15–25, wherein the external monitoring device further comprises:
   means for periodically deriving and conveying the ambient signal value to the implantable medical device, and the conveyed ambient signal value is used in the derivation of a plurality of relative physiologic signal values in the period between successive conveyances of the ambient signal value to the implantable medical device.

29. An implantable medical device method for deriving relative physiologic signal value data for use by and/or storage within an implantable medical device implanted within a patient's body comprising the steps of:
   providing an external monitoring device associated with the patient, and in the external monitoring device,
      periodically sensing an ambient state or condition outside the body affecting a sensed physiologic state or condition within the body and deriving an ambient signal value from each sensed ambient state or condition;
      storing a plurality of the ambient signal values; and
      conveying the plurality of ambient signal values from the external monitoring device to the implantable medical device; and
   in the implantable medical device implanted in the patient's body,
      periodically sensing a physiologic state or condition within the body of the patient and deriving an absolute physiologic signal value from each sensed physiologic state or condition;
      storing a plurality of the absolute physiologic signal values;
      receiving the plurality of ambient signal values conveyed from the external monitoring device; and
      combining the plurality of derived absolute physiologic signal values and the plurality of conveyed ambient signal values to derive a plurality of relative physiologic signal values therefrom.

30. The method of claim 29, wherein the implantable medical device comprises implantable device memory and further comprising the step of:
   storing said plurality of relative physiologic signal values as relative physiologic signal value data in the implantable medical device memory.

31. The method of claim 29, wherein the implantable medical device comprises an implantable monitor having implantable device memory and further comprising the step of:
   storing said plurality of relative physiologic signal values as relative physiologic signal value data in the implantable medical device memory.

32. The method of claim 29, wherein the implantable medical device comprises an implantable monitor having implantable device memory and data conveying means for conveying data stored in the implantable memory to an external memory device further comprising the steps of:

storing said plurality of relative physiologic signal values as relative physiologic signal value data in the implantable medical device memory; and activating said data conveying means to convey the relative physiological signal value data stored in the implantable memory to an external medical device.

33. The method of claim 29, wherein the implantable medical device comprises implantable device memory and a therapy delivery system for delivering a therapy to the patient and further comprising the steps of:

storing said predetermined number of relative physiologic signal values as relative physiologic signal value data in the implantable medical device memory; and employing the relative physiologic signal values to control the delivery of the therapy by the implantable medical device.

34. The method of claim 29, wherein the implantable medical device comprises a therapy delivery system for delivering a therapy to the patient and further comprising the step of:

controlling the delivery of the therapy by the implantable medical device as a function of the relative physiologic signal value data.

35. The method of any of the preceding claims 29–34, wherein the physiologic state or condition comprises the blood pressure of the patient, the sensed absolute physiologic signal value is absolute blood pressure value, the ambient state or condition comprises barometric pressure affecting the patient and the absolute pressure value, the relative physiologic signal value is relative blood pressure; and the step of combining the derived absolute physiologic signal value and the conveyed ambient signal value comprises subtracting the barometric pressure from the absolute blood pressure.

36. The method of any of the preceding claims 29–34, wherein the physiologic state or condition comprises the blood temperature of the patient, the sensed absolute physiologic signal value is absolute blood temperature, the ambient state or condition comprises systemic patient temperature affected by fever or ambient conditions, the relative physiologic signal value is relative blood temperature; and the step of combining the derived absolute physiologic signal value and the conveyed ambient signal value comprises subtracting the ambient temperature from the absolute blood temperature.

37. A system for deriving relative physiologic signal values from absolute physiologic signal values for use by and/or storage within an implantable medical device comprising:

an external monitoring device associated with the patient comprising, external sensing means for periodically sensing an ambient state or condition outside the body affecting a sensed physiologic state or condition within the body;

signal processing means coupled with said external sensing means for deriving an ambient signal value from the sensed ambient state or condition;

memory means for storing a plurality of the ambient signal values; and signal conveying means for conveying the plurality of ambient signal values from the external monitoring device to the implantable medical device; and the implantable medical device implanted within a patient's body comprising, implantable sensing means for periodically sensing a physiologic state or condition within the body of the patient;

signal processing means coupled with said implantable sensing means for deriving an absolute physiologic signal value from the sensed physiologic state or condition;

receiving means for receiving the plurality of ambient signal values conveyed from said signal conveying means; and means for combining the plurality of derived absolute physiologic signal values with the plurality of sensed ambient signal values to derive a plurality of relative physiologic signal values therefrom.

38. The system of claim 37, wherein the implantable medical device further comprises:

implantable device memory; and means for storing said plurality of relative physiologic signal values as relative physiologic signal value data in the implantable medical device memory.

39. The system of claim 37, wherein the implantable medical device comprises an implantable monitor further comprising:

implantable device memory; and means for storing a plurality of relative physiologic signal values as relative physiologic signal value data in the implantable medical device memory.

40. The system of claim 37, wherein the implantable medical device comprises an implantable monitor fuirther comprising:

implantable device memory;

means for storing a plurality of relative physiologic signal values as relative physiologic signal value data in the implantable medical device memory;

data conveying means for conveying data stored in the implantable memory to an external memory device; and means for activating said data conveying means to convey the relative physiological signal value data stored in the implantable memory to said external medical device.

41. The system of claim 37, wherein the implantable medical device further comprises a therapy delivery system for delivering a therapy to the patient further comprising:

implantable device memory;

means for storing a predetermined number of relative physiologic signal values as relative physiologic signal value data in the implantable medical device memory; and means for employing the relative physiologic signal values to control the delivery of the therapy by the implantable medical device.

42. The system of claim 37, wherein the implantable medical device comprises a therapy delivery system for delivering a therapy to the patient further comprising:

means for controlling the delivery of the therapy by the implantable medical device as a function of the plurality of relative physiologic signal values.

43. The system of any of the preceding claims 37–42, wherein the physiologic state or condition comprises the blood pressure of the patient, the sensed absolute physiologic signal value is absolute blood pressure value, the ambient state or condition comprises barometric pressure affecting the patient and the absolute pressure value, the relative physiologic signal value is relative blood pressure; and the means for combining the plurality of derived absolute physiologic signal values with the plurality of sensed ambient signal values to derive a plurality of relative physiologic signal values therefrom comprises means for subtracting the barometric pressure value from the absolute blood pressure value to derive a relative blood pressure value.

44. The system of any of the preceding claims 37–42, wherein the physiologic state or condition comprises the blood temperature of the patient, the sensed absolute physiologic signal value is absolute blood temperature, the ambient state or condition comprises systemic patient temperature affected by fever or ambient conditions, the relative physiologic signal value is relative blood temperature; and the means for combining the plurality of derived absolute physiologic signal values with the plurality of sensed ambient signal values to derive a plurality of relative physiologic signal values therefrom comprises means for subtracting the ambient temperature from the absolute blood temperature to derive a relative blood temperature.

* * * * *